United States Patent [19]

Sohda et al.

[11] Patent Number: 5,280,022

[45] Date of Patent: Jan. 18, 1994

[54] BISPHOSPHONIC ACID DERIVATIVES, THEIR PRODUCTION AND USE

[75] Inventors: Takashi Sohda, Takatsuki; Shigehisa Taketomi, Ikeda, both of Japan

[73] Assignee: Takeda Chemical Industries, Ltd., Osaka, Japan

[21] Appl. No.: 809,328

[22] Filed: Dec. 18, 1991

[30] Foreign Application Priority Data

| Dec. 19, 1990 | [JP] | Japan | 2-412338 |
| Dec. 19, 1990 | [JP] | Japan | 2-412542 |
| Oct. 29, 1991 | [JP] | Japan | 3-283073 |
| Nov. 1, 1991 | [JP] | Japan | 3-287984 |

[51] Int. Cl.$^5$ .............................. A61K 31/66
[52] U.S. Cl. ...................... 514/114; 558/158;
 514/85; 514/86; 514/89; 514/80; 514/92;
 544/232; 544/337; 544/243; 546/22; 546/24;
 546/23; 548/113
[58] Field of Search ................. 514/114; 558/158

[56] References Cited

U.S. PATENT DOCUMENTS

| 4,096,208 | 6/1978 | Dursch et al. | 558/158 |
| 4,719,203 | 1/1988 | Boises et al. | 558/158 |
| 4,746,654 | 5/1988 | Breliere et al. | 514/108 |
| 4,933,742 | 6/1990 | Isomura | 558/158 |
| 4,970,335 | 11/1990 | Isomura | 558/158 |
| 5,036,058 | 7/1991 | Jaeggi | 514/102 |
| 5,041,428 | 8/1991 | Isomura et al. | 558/158 |

FOREIGN PATENT DOCUMENTS

| 0151072 | 8/1935 | European Pat. Off. |
| 0230068 | 7/1987 | European Pat. Off. |
| 0243173 | 10/1987 | European Pat. Off. |
| 0282309 | 9/1988 | European Pat. Off. |
| 0282320 | 9/1988 | European Pat. Off. |
| 0298553 | 1/1989 | European Pat. Off. |
| 0325482 | 7/1989 | European Pat. Off. |
| 0337706 | 10/1989 | European Pat. Off. |
| 0387194 | 9/1990 | European Pat. Off. |
| 54-37829 | 3/1979 | Japan |
| 1-258695 | 10/1989 | Japan |
| 1-308290 | 12/1989 | Japan |
| 2-184 | 1/1990 | Japan |
| 2-185 | 1/1990 | Japan |
| 445675 | 10/1974 | U.S.S.R. | 558/158 |

OTHER PUBLICATIONS

Thompson et al. Jour. Bone & Min. Res. vol. 5 No. 3 pp. 279-286 (1990).
Burger, "Medicinal Chemistry" 2d Ed Interscience, NY, 1960 p. 42.
F. Suzuki et al., Chemical Abstracts, 91(13): 103762h (Sep. 24, 1979).

*Primary Examiner*—Donald G. Daus
*Attorney, Agent, or Firm*—Wegner, Cantor, Mueller & Player

[57] ABSTRACT

A compound of the formula (I):

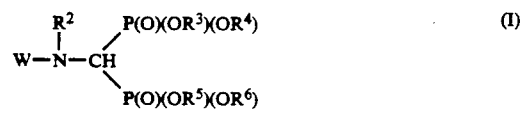

wherein W is a group of the formula:

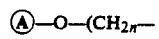

wherein Ⓐ is a cyclic group which may be substituted, n is an of 2 to 10, or W is a group of the formula:

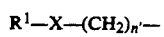

wherein $R^1$ is an alkyl group which may be substituted, X is an oxygen atom or a sulfur atom which may be oxidized, n' is an integer of 4 to 10; $R^2$ is a hydrogen atom or a lower alkanoyl group; $R^3$, $R^4$, $R^5$ and $R^6$ are the same or different and are a hydrogen atom or a lower alkyl group, or a salt thereof, is useful as a bone resorption inhibitor.

9 Claims, No Drawings

BISPHOSPHONIC ACID DERIVATIVES, THEIR PRODUCTION AND USE

FIELD OF THE INVENTION

The present invention relates to alkylaminomethylenebisphosphonic acid derivatives, lower alkyl esters thereof and pharmaceutically acceptable salts thereof, which are useful as a medicament having bone resorption inhibitory activity as well as antiinflammatory activity, antirheumatic activity and the like, and to pharmaceutical compositions containing them as active ingredients.

PRIOR ART

Substituted aminomethylenebisphosphonic acid derivatives wherein the substituent is 3-methoxypropyl, 2-ethoxyethyl and 2-ethylthioethyl are specifically described in Japanese Patent Laid Open Publication No. 37829/1979. Although these compounds are described as being usable as herbicides and fungicides, there is no suggestion about the utility thereof as drugs.

Although various bisphosphonic acid derivatives have heretofore been produced for use as bone resorption inhibitors (Japanese Patent Laid Open Publication Nos. 258695/1989, 308290/1989 (corresponding to EP-A-325,482) 184/1990 and 185/1990 (corresponding to EP-A-282,320) and EP-A-0337706), none of them are as satisfactory as desired in terms of activity and side effects.

The present invention relates to (1) novel bisphosphonic acid derivatives having excellent bone resorption inhibitory activity and (2) bone resorption inhibitory compositions containing said novel compounds or known bisphosphonic acid derivatives that the present inventors first have found to be useful as possessing bone resorption inhibitory activity.

The present inventors have studied intensively to develop bisphosphonic acid derivatives which are more useful as bone resorption inhibitors. As a result, it has been found that bisphosphonic acid derivatives of the following formula (I) as shown hereinafter can directly affect the bone to manifest excellent bone resorption inhibitory activity.

SUMMARY OF THE INVENTION

The compound according to the present invention is structurally characterized in that it has a hydroxy group substituted with a cyclic group; alkoxy, alkylthio, alkylsulfinyl, or alkylsulfonyl group on the alkyl side chain of the alkylamino group, and the compound can be used as a bone resorption inhibitor.

According to the present invention, there is provided, (1) a compound of the formula (I):

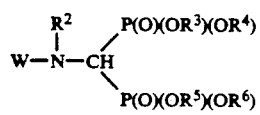
(I)

wherein W is a group of the formula:

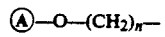

wherein Ⓐ is a cyclic group which may be substituted, n is an integer of 2 to 10, or W is a group of the formula:

$$R^1-X-(CH_2)_{n'}-$$

wherein $R^1$ is an alkyl group which may be substituted, X is an oxygen atom or a sulfur atom which may be oxidized, n' is an integer of 4 to 10; $R^2$ is a hydrogen atom or a lower alkanoyl group; $R^3$, $R^4$, $R^5$ and $R^6$ are the same or different and are a hydrogen atom or a lower alkyl group, or a salt thereof.

(2) a bone resorption inhibitor which comprises a compound of the formula (II):

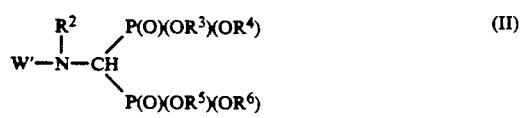
(II)

wherein W' is a group of the formula:

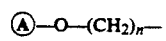

wherein each is as defined above, or W' is a group of the formula:

$$R^1-X-(CH_2)_n-$$

wherein each symbol is as defined above; the other symbols are as defined above, or a salt thereof, and (3) a process for producing the compound of the formula (I) or a salt thereof which comprises reacting an amine derivative of the formula (III):

$$W'''-NH_2 \quad (III)$$

wherein W''' is a group of the formula:

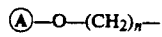

wherein each symbol is as defined above, or W''' is a group of the formula:

$$R^1-Y-(CH_2)_{n'}-$$

wherein Y is an oxygen or sulfur atom and the other symbols are as defined above, with an orthoformate derivative of the formula (IV):

$$CH(OR^7)_3 \quad (IV)$$

wherein $R^7$ is a lower alkyl group, and a phosphite derivative of the formula (V):

(V)

wherein $R^8$, $R^9$, $R^{10}$ and $R^{11}$ are the same or different and are a lower alkyl group, and then optionally subjecting the resultant compound to acylation, oxidation and/or hydrolysis.

DETAILED DESCRIPTION OF THE INVENTION

In the above-mentioned formula, the cyclic group in the cyclic group which is represented by (A), includes aromatic or non-aromatic homo- and cyclic groups. Examples of the aromatic homo-cyclic group include $C_{6-14}$ aromatic hydrocarbon groups such as phenyl, naphthyl, anthryl, etc. Preferable examples of the aromatic heterocyclic group include 5- or 6-membered aromatic heterocyclic groups having 1 to 4 nitrogen atoms, oxygen atoms and/or sulfur atoms (e.g. pyridyl, pyrimidinyl, pyridazinyl, furyl, thienyl, imidazolyl, thiazolyl, oxazolyl, isoxazolyl, thiadiazolyl, pyrazinyl, etc.) and condensed aromatic heterocyclic groups (e.g. benzothiazolyl, benzoxazolyl, benzimidazolyl, s-triazolo[1,2-a]pyridyl, imidazo[1,2-b]pyrazinyl, imidazo[1,2-a]pyridyl, etc.). Preferable examples of the non-aromatic heterocyclic group include 5- or 6-membered non-aromatic heterocyclic groups having 1 to 4 nitrogen atoms, oxygen atoms and/or sulfur atoms (e.g. thiazolin-2-yl, oxazolin-2-yl, etc.). Preferable examples of the non-aromatic homocyclic group include $C_{3-7}$ cycloalkyl such as cyclopropyl, cyclobutyl, cyclopentyl, cyclohexyl, cycloheptyl, etc.

Examples of substituents of these cyclic groups include a halogen atom, nitro group, an optionally substituted alkyl group, an optionally substituted hydroxyl group and an optionally substituted thiol group. One to four, preferably one or two, of these substituents, which may be the same or different, can take any position on the cyclic group.

The term "halogen atom" used herein includes fluorine, chlorine, bromine and iodine. The alkyl in the optionally substituted alkyl group is preferably, a $C_{1-7}$ straight-chain or branched alkyl group such as methyl, ethyl, propyl, isopropyl, butyl, isobutyl, secbutyl, tert-butyl, pentyl, isopentyl, neopentyl, hexyl, heptyl or the like; or a $C_{3-7}$ cycloalkyl group such as cyclopropyl, cyclobutyl, cyclopentyl, cyclohexyl, or cycloheptyl or the like. These groups may be substituted with one to three substituents such as a halogen atom (e.g. fluorine, chlorine, bromine or iodine), hydroxyl group, $C_{1-6}$ alkoxy group (e.g. methoxy, ethoxy, propoxy, butoxy, hexyloxy, etc.) and the like.

The examples of the substituted alkyl group include trifluoromethyl, 2,2,2-trifluoroethyl, trichloromethyl, hydroxymethyl, 2-hydroxyethyl, 2-methoxyethyl and the like.

The substituent of the substituted hydroxyl group is exemplified by a protecting group for a hydroxyl group, for example, alkoxy, alkenyloxy, aralkyloxy, acyloxy and aryloxy. Examples of the alkoxy include $C_{1-6}$ straight-chain or branched alkoxy groups (e.g. methoxy, ethoxy, propoxy, isopropoxy, butoxy, isobutoxy, sec-butoxy, tert-butoxy, pentoxy, isopentoxy, neopentoxy, hexyloxy, etc.) and $C_{4-6}$ cycloalkoxy groups (e.g. cyclobutoxy, cyclopentoxy, cyclohexyloxy, etc.) and examples of the alkenyloxy, preferably include $C_{2-6}$ alkenyloxy groups (e.g. allyloxy, crotyloxy, 2-pentenyloxy, 3-hexenyloxy, 2-cyclopentenylmethoxy, etc). As the aralkyloxy group, preferably, $C_{6-19}$ aralkyloxy groups, more preferably, $C_{6-14}$ aryl-$C_{1-4}$ alkyloxy groups (e.g. benzyloxy, phenethyloxy, etc.) can be used. As the acyloxy group, preferably, alkanoyloxy groups, for example, $C_{2-7}$ alkanoyloxy groups (e.g. acetyloxy, propionyloxy, n-butyryloxy, iso-butyryloxy, hexanoyloxy, etc.) can be used. As the aryloxy group, preferably, $C_{6-14}$ aryloxy groups (e.g. phenoxy, biphenyloxy, etc.) can be used. These groups may be further substituted with one to three substituents such as the above-mentioned halogen atom, hydroxyl group and $C_{1-6}$ alkoxy groups and the like. Specific examples of the substituted hydroxyl group include trifluoromethoxy, difluoromethoxy, 2,2,2-trifluoroethoxy, 2-methoxyethoxy, 4-chlorobenzyloxy, 2-(3,4-dimethoxyphenyl)ethoxy and the like.

The substituted thiol group is a thiol group having a suitable substituent, particularly, a protecting group for a thiol group, for example, alkylthio, aralkylthio or acylthio. As the alkylthio group, preferably, a $C_{1-6}$ straight-chain or branched alkylthio group (e.g. methylthio, ethylthio, propylthio, isopropylthio, butylthio, isobutylthio, sec-butylthio, tert-butylthio, pentylthio, isopentylthio, neopentylthio, hexylthio, etc.), and a $C_{4-7}$ cycloalkylthio group (e.g. cyclobutylthio, cyclopentylthio, cyclohexylthio, cycloheptylthio, etc.) can be used. As the aralkylthio group, preferably, a $C_{7-19}$ aralkylthio group, more preferably, a $C_{6-14}$ aryl-$C_{1-4}$ alkylthio group such as benzylthio or phenethylthio can be used. As the acylthio group, preferably, $C_{2-7}$ alkanoylthio (e.g. acetylthio, propionylthio, n-butyrylthio, iso-butyrylthio, hexylthio, etc.) can be used. These groups may be further substituted with one to three substituents such as the above-mentioned halogen atom, hydroxyl group, $C_{1-6}$ alkoxy group and the like. Specific examples of the substituted thiol group include trifluoromethylthio, difluoromethylthio, 2,2,2-trifluoroethylthio, 2-methoxyethylthio, 4-chlorobenzylthio, 3,4-dichlorobenzylthio, 4-fluorobenzylthio, 2-(3,4-dimethoxyphenyl)ethylthio, etc.

Specific examples of the substituted aromatic hydrocarbon group include 4-chlorophenyl, 2-fluorophenyl, 4-nitrophenyl, 3-methylphenyl, 3-trifluoromethylphenyl, 5,6,7,8-tetrahydro-2-naphthyl, 4-methoxyphenyl, 3,4-methylenedioxyphenyl, 4-(4-chlorobenzyloxy)phenyl, 4-acetoxyphenyl, 3methylthiophenyl, 2-acetamidophenyl, 6-methoxy-2naphthyl, etc.

Specific examples of the substituted aromatic heterocyclic group include 2-chloropyridyl, 5-nitro-2-pyridyl, 3-hydroxy-2-pyridyl, 6-methoxy-2-pyridyl, 2-methyl-4-pyridyl, 4-methyl-2-pyrimidinyl, 4-hydroxy-6-methylpyrimidinyl, 5-trifluoromethyl-2-benzothiazolyl, 5-chloro-2-triazolo[1,2-a]pyrid-3-yl, etc.

Specific examples of the substituted heterocyclic group include 5-phenyl-2-thiazolin-2-yl, 5-methyl-2-oxazolin-2-yl, etc.

(A) is, preferably, a phenyl, pyridyl, pyrimidinyl or pyridazinyl group, which is unsubstituted or substituted with a halogen atom, a $C_{1-6}$ alkyl group or a $C_{1-6}$ alkoxy group.

As the alkyl of the alkyl group which may be substituted, which is represented by $R^1$, is preferable a $C_{1-7}$ straight-chain or branched alkyl group such as methyl, ethyl, propyl, isopropyl, butyl, isobutyl, secbutyl, tert-butyl, pentyl, isopentyl, neopentyl, hexyl, heptyl or the like. These groups may be substituted with 1 to 3 substituents such as halogen (e.g. fluorine, chlorine, bromine, iodine), hydroxyl, an optionally substituted $C_{6-14}$ aromatic hydrocarbon group such as phenyl, naphthyl, anthryl, etc., optionally substituted 5- or 6-membered aromatic heterocyclic group having 1 to 4 nitrogen atoms, oxygen atoms and/or sulfur atoms (e.g. pyridyl, pyrimidinyl, furyl, thienyl, imidazolyl, thiazolyl, oxazolyl, isoxazolyl, thiadiazolyl, pyrazolyl, pyrazinyl, triazolyl, etc.), an optionally substituted condensed aromatic heterocyclic group (e.g. benzothiazolyl, benzoxazolyl, benzimidazolyl, etc.), $C_{1-6}$ alkoxy group (e.g. methoxy, ethoxy, propoxy, butoxy, hexyloxy) and carboxyl which may be esterified. More preferably, $R^1$ is a $C_{1-7}$ straight-chain or branched alkyl group or a $C_{1-7}$ straight-chain or branched alkyl substituted with phenyl.

Examples of substituents of said $C_{6-14}$ aromatic hydrocarbon group, 5- or 6-membered aromatic heterocyclic group or condensed aromatic heterocyclic group include a halogen atom; nitro group; a $C_{1-7}$ straight-chain or branched alkyl or $C_{3-7}$ cycloalkyl group which may be substituted with 1 to 3 substituents such as a halogen atom, hydroxyl group and $C_{1-6}$ alkoxy group; a hydroxy group; a $C_{1-6}$ straight-chain or branched alkoxy group; a $C_{4-6}$ cycloalkoxy group; a $C_{2-6}$ alkenyloxy group; a $C_{6-14}$ aryl-$C_{1-4}$ alkoxy group; a $C_{2-7}$ alkanoyloxy group; a $C_{6-14}$ aryloxy group; a thiol group; a $C_{1-6}$ straight-chain or branched alkylthio group; a $C_{4-7}$ cycloalkylthio group; a $C_{6-14}$ aryl-$C_{1-4}$ alkylthio group; $C_{2-7}$ alkanoylthio group.

Examples of the esterified carboxyl group are a group of the formula —COOR (R is an ester residue). Examples of the ester residues of R are $C_{1-7}$ straight-chain or branched alkyl, $C_{3-7}$ cycloalkyl, $C_{7-10}$ aralkyl (e.g. phenyl-$C_{1-4}$ alkyl), $C_{2-10}$ alkenyl, $C_{6-14}$ aryl (e.g. phenyl, naphthyl, anthryl, phenanthryl), etc.

Specific examples of the substituted alkyl represented by $R^1$ include trifluoromethyl, 2,2,2-trifluoroethyl, trichloromethyl, hydroxymethyl, 2-hydroxyethyl, benzyl, 4-(2-methoxyethyl)benzyl, 4-chlorobenzyl, 2-phenylethyl, 2-pyridylmethyl, 2-methyl-4-thiazolylmethyl, etc.

The lower alkanoyl group represented by $R^2$ is preferably an $C_{1-6}$ alkyl-carbonyl group, such as acetyl, propionyl, butyryl, isobutyryl, valeryl, pivaloyl, hexanoyl, etc., or a sulfonic acyl group having a $C_{1-6}$ hydrocarbon moiety (e.g. methanesulfonyl, ethanesulfonyl, propanesulfonyl, hexanesulfonyl, benzenesulfonyl).

The lower alkyl groups represented by $R^3$, $R^4$, $R^5$, $R^6$, $R^7$, $R^8$, $R^9$, $R^{10}$ and $R^{11}$, include $C_{1-4}$ straight-chain or branched alkyl groups, such as methyl, ethyl, propyl, butyl, isopropyl, isobutyl, tert-butyl and the like.

The sulfur atom which may be oxidized, which is represented by X, forms a thioether, sulfinyl or sulfonyl linkage between $R^1$ and $(CH_2)_n$ or $(CH_2)_{n'}$.

The symbol n stands for a whole number of 2 through 10 while n' means a whole number of 4 through 10. The symbol n is preferably 3, 4 or 5 and n' is preferably 4 or 5, more preferably, n and n' are 4.

W and W' are preferably a group of the formula (A)—O—$(CH_2)_n$— wherein each symbol is as defined above.

The compound of the formulas (I) and (II) or a salt thereof can be produced by the process described in Japanese Patent Laid Open Publication No. 37829/1979 or by per se known method.

For example, the compound (I) or a salt thereof can be produced by the following processes. The salts of the compounds described hereinafter may be the same as those described with respect to the compound (I).

PROCESS A

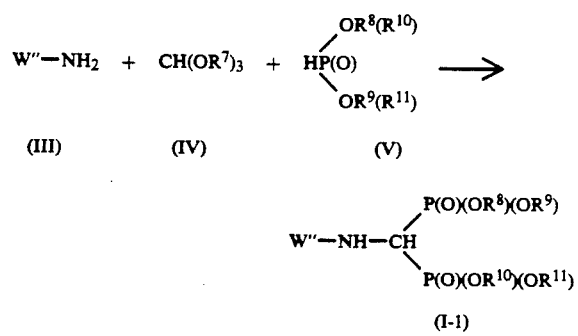

[wherein W''' is a group of the formula: (A)—O—$(CH_{2n}$— wherein each symbol is defined hereinbefore, or W''' is a group of the formula: $R^1$—Y—$(CH_2)_{n'}$— wherein Y is an oxygen atom or a sulfur atom and $R^1$ and n' are as defined above; the other symbols are as defined hereinbefore]

PROCESS B

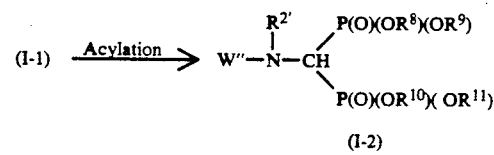

[wherein $R^{2'}$ is a lower acyl group; each symbol is as defined hereinbefore]

PROCESS C

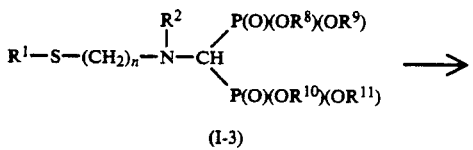

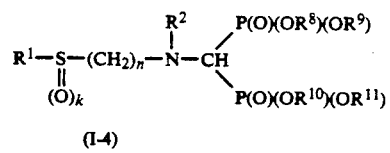

[wherein k is 1 or 2; the other symbols are as defined hereinbefore]

PROCESS D

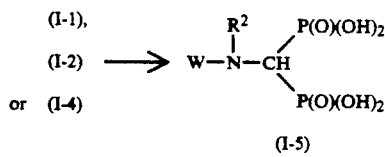

[wherein each symbol is as defined hereinbefore]

PROCESS E-1

(I-1)→a bisphosphonic acid diester.

PROCESS E-2

(I-1), (I-2) or (I-4)→a bisphosphonic acid mono- or tri-ester.

The respective processes are now described in detail.

PROCESS A

This process comprises reacting an amine derivative (VI) with an orthoformate derivative (IV) and a phosphite derivative (V) to give a bisphosphonate derivative (I-1). The relative amount of the compounds (VI), (V) and (IV) may be 2:4:1. The reaction may be carried out in a conventional solvent but use of the solvent is not essential. This reaction is usually conducted at 80° C. to 200° C., preferably at 100° C. to 170° C. for 10 minutes to 15 hours.

PROCESS B

This process comprises acylating the compound (I-1) prepared in accordance with Process A. This acylation is carried out by reacting the compound (I-1) with 1 to 2 equivalents of an acylating agent, i.e. an acid corresponding to the lower alkanoyl group represented by $R^2$ or its reactive derivative (acid anhydride, acid halide, etc.) in a solvent or without using a solvent. The solvent may for example be benzene, xylene, toluene, chloroform, dichloromethane, ethyl acetate, ether, tetrahydrofuran, or the like. The reaction is conducted at 0° C. to 100° C. for 30 minutes to 10 hours.

PROCESS C

This oxidation reaction is carried out by the conventional procedure using an oxidizing agent. The oxidizing agent is preferably a mild oxidizing agent which does not substantially affect the skeletal structure of compound (I-3), such as m-chloroperbenzoic acid, hydrogen peroxide, peresters, sodium metaperiodate, etc.

This reaction is conducted in an organic solvent which does not adversely interfere with the reaction.

As the solvent, for example, a halogenated hydrocarbon (e.g. methylene chloride, chloroform, dichloroethane, etc.), hydrocarbon (e.g. benzene, toluene, etc.), or alcohol (e.g. methanol, ethanol, propanol, etc.) or a mixed solvent thereof can be used.

When an equimolar amount or less of the oxidizing agent is used based on the compound (I-3), the compound of formula (I-4) wherein k is 1 is preferentially produced. When more than an equimolar amount of the oxidizing agent is used, the compound (I-4) wherein k is 1 is further oxidized to produce the compound (I-4) wherein k is 2.

This reaction proceeds at a temperature below room temperature (20° C. to 30° C.). Preferably, the reaction temperature is in the range of about −50° C. to 20° C.

The reaction time is about 30 minutes to 10 hours.

PROCESS D

In this process, the bisphosphonate (I-1), (I-2) or (I-4), synthesized by process A, B or C as the case may be, is hydrolyzed to the corresponding bisphosphonic acid (I-5).

This reaction is conducted using an inorganic acid, such as hydrochloric acid, hydrobromic acid, etc., or a halotrialkylsilane in a solvent which does not interfere with the reaction.

When an inorganic acid such as hydrochloric acid or hydrobromic acid or the like is used, the solvent may be alcohol, such as methanol, ethanol, 2-methoxyethanol, ethylene glycol, propanol, butanol, etc., acetic acid or water or mixed solvent thereof. The acid is generally used in large excess, the reaction temperature is in the range of 0° C. to 150° C., preferably 30° C. to 100° C., and the reaction time is 1 to 50 hours.

When a halogenated alkylsilane such as chlorotrimethylsilane, bromotrimethylsilane, iodotrimethylsilane, etc. is used, a halogenated hydrocarbon such as carbon tetrachloride, chloroform, dichloromethane, 1,2-dichloroethane, 1,1,2,2-tetrachloroethane, etc., or acetonitrile, or a mixed solvent thereof can be used as a solvent.

The proportion of the halogenated alkylsilane is 4 to 10 equivalents, preferably 4 to 8 equivalents, based on the compound (I-1), (I-2) or (I-4). The reaction temperature is in the range of −30° C. to 100° C., preferably −10° C. to 50° C., and the reaction time is 30 minutes to 100 hours.

PROCESS E-1

This process comprises subjecting bisphosphonic acid tetraester (I-1) produced by Process A to hydrolysis with a base to give bisphosphonic acid diester.

The proportion of the base (sodium hydroxide, potassium hydroxide, etc.) is 2 to 2.2 molar equivalents, based on the compound (I-1), and the hydrolysis is conducted in an aqueous solvent in accordance with a conventional method.

PROCESS E-2

In this process, the bisphosphonic acid tetraester (I-1), (I-2) or (I-4), produced by process A, process B or process C, is subjected to partial hydrolysis with a halogenated alkylsilane to give bisphosphonic acid mono- or tri-ester.

The proportion of the halogenated alkylsilane (chlorotrimethylsilane, bromotrimethylsilane, iodotrimethylsilane, etc.) is, in the case of producing triester, 1 to 1.2 molar equivalent, and, in the case of producing monoester, 3 to 3.3 molar equivalents, based on the compound (I-1) or (I-2), and the reaction is conducted in accordance with the process D.

The bisphosphonic acid derivative (I) thus obtained can be isolated and purified according to known means for separation and purification, for example, by concentration, concentration under reduced pressure, solvent extraction, precipitation, recrystallization, chromatography and the like.

For conversion of such bisphosphonic acid to a salt, the acid is treated with a base such as potassium hydroxide, sodium hydroxide, sodium methoxide, ammonia or an organic amine in the per se conventional manner.

The starting compound (III) of the present invention can be prepared by the following and other processes.

PROCESS F

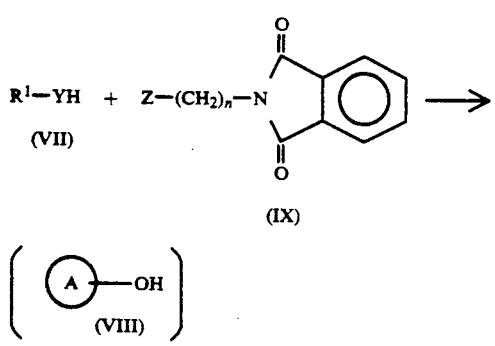

(IX)

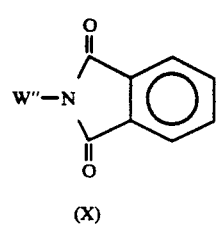

(X)

[wherein Z is a leaving group; the other symbols are as defined hereinbefore]

This process comprises reacting the compound (VII) or (VIII) with the compound (IX) in the presence of a base to give the compound (X). The leaving group represented by Z includes halogen atoms, preferably chlorine, bromine and iodine, hydroxyl activated in the form of an ester, organic sulfonic acid residues (e.g. p-toluenesulfonyloxy), $C_{1-4}$ alkylsulfonyloxy (e.g. methanesulfonyloxy) and organic phosphoric acid residues such as diphenylphosphoryloxy, dibenzylphosphoryloxy, dimethylphosphoryloxy and so on. The reaction of the compounds (VII) or (VIII) with (IX) is conducted in an appropriate solvent. This solvent includes aromatic hydrocarbons such as benzene, toluene, xylene, etc., ethers such as dioxane, tetrahydrofuran, dimethoxyethane, etc., alcohols such as methanol, ethanol, propanol, etc., ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone, and a mixed solvent thereof. The reaction of the compounds (VII) or (VIII) with (IX) is carried out in the presence of an appropriate base, which may for example be an alkali metal salt such as sodium hydroxide, potassium hydroxide, potassium carbonate, sodium carbonate, sodium hydrogen carbonate, etc., sodium hydride, potassium hydride or an amine such as pyridine, triethylamine, N,N-dimethylaniline and so on. The preferred proportion of the base is about 1 to 5 moles based on the compound (VII) or (VIII). This reaction is usually conducted at $-20°$ C. to $150°$ C. and preferably at about $0°$ C. to $130°$ C. for 1 to 10 hours.

PROCESS G

Production of the Starting Material Compound (X)

First-Stage Reaction

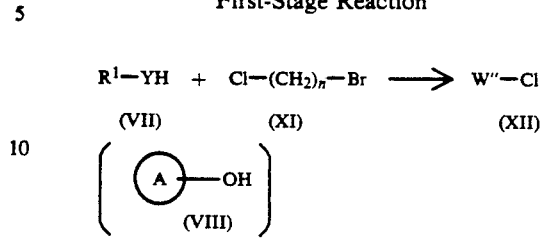

[wherein each symbol is as defined hereinbefore]

In this process, the compound (VII) or (VIII) is reacted with the compound (XI) in a substantially equimolar ratio in the presence of a base to give the compound (XII) in the first place. This reaction of the compounds (VII) or (VIII) with (XI) is carried out in the same manner as Process F.

Second-Stage Reaction

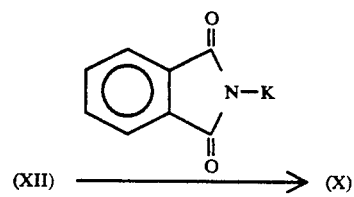

In this process, the compound (XII) prepared by the first-stage reaction of Process G is reacted with potassium phthalimide in a substantially equimolar ratio to give the compound (X). This reaction between the compound (XII) and potassium phthalimide is carried out in an appropriate solvent. The solvent includes aromatic hydrocarbons such as benzene, toluene, xylene, etc.; ethers such as dioxane, tetrahydrofuran, dimethoxyethane, etc.; alcohols such as methanol, ethanol, propanol, etc.; and such other solvents as ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone, and a mixed solvent thereof. This reaction is usually conducted at $-20°$ C. to $150°$ C. and preferably about $30°$ C. to $130°$ C. for 1 to 10 hours.

PROCESS H

Production of the Compound (III)

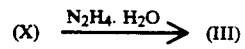

This process comprises reacting the compound (X) prepared by Processes F and G with hydrazine hydrate to give a compound of the formula (III). The reaction between the compound (X) and hydrazine hydrate is carried out in an appropriate solvent. The solvent includes aromatic hydrocarbons such as benzene, toluene, xylene, etc.; ethers such as dioxane, tetrahydrofuran, dimethoxyethane, etc.; alcohols such as methanol, ethanol, propanol, etc., and such other solvents as N,N-dimethylformamide, dimethyl sulfoxide, chloroform, dichloromethane, 1,2-dichloroethane, 1,1,2,2-tetrachloroethane and a mixed solvent thereof. The proportion of hydrazine hydrate is 1 to 10 mole equivalents, preferably 1.2 to 5 mole equivalents, based on the compound (X). This reaction is usually conducted at −20° C. to 150° C. and preferably at about 0° C. to 100° C. for 1 to 10 hours.

The compound (III) thus obtained can be isolated and purified by the known workup procedures such as concentration, concentration under reduced pressure, solvent extraction, crystallization, recrystallization, redistribution, chromatography and so on.

The preferred salts of the compound (I) are pharmaceutically acceptable salts, e.g. inorganic salts including alkali metal salts such as sodium salt, potassium salt, etc., alkaline earth metal salts such as calcium salt, magnesium salt, ammonium salts, etc.; organic base salts such as methylamine salt, ethylamine salt, propylamine salt, isopropylamine salt, butylamine salt, tert-butylamine salt, dimethylamine salt, diethylamine salt, trimethylamine salt, triethylamine salt, pyridine salt, picoline salt, dicyclohexylamine salt, N,N-dibenzylethylenediamine salt, etc.; organic acid addition salts such as formate, acetate, trifluoroacetate, maleate, tartrate, methanesulfonate, benzenesulfonate, toluenesulfonate, etc.; inorganic acid addition salts such as hydrochloride, hydrobromide, sulfonate, etc.; and amino acid salts such as glutamic acid and so on.

The compound (I) or a salt thereof provided by the present invention has bone resorption inhibitory activity and, as such, inhibit the loss of bone caused by bone resorption. The compound (I) has low toxicity and little side effect.

Therefore, the compound (I) of the invention can be used in the prevention or treatment of osteoporosis in mammalian animals (e.g. mouse, rat, rabbit, dog, cat, cattle, pig, man, etc.).

For administration of the compound to human beings, the oral and other routes can be selectively employed. Compositions for oral administration may be solid or liquid, and specifically tablets (including dragees and film-coated tablets), pills, granules, powders, capsules (including soft capsules), syrups, emulsions, suspensions etc. may be mentioned. Such compositions can be manufactured by the per se known methods and may contain the carrier or excipient which is commonly employed in the pharmaceutical practice. Thus, lactose, starch, sucrose, magnesium stearate, etc. may be mentioned as examples of the carrier/excipient for powders or tablets.

Compositions for non-oral administration include injections and suppositories, for instance, and the injections include subcutaneous, intradermal and intramuscular injections, for instance. Such injections can be manufactured by the per se known method, viz. suspending or emulsifying compound (I) in a sterile aqueous or oily vehicle which is commonly used in the manufacture of injections. The aqueous vehicle for injection includes, among others, physiological saline, other isotonic solutions, etc., and, if necessary, may contain an appropriate suspending agent such as carboxymethylcellulose sodium, nonionic surfactants and so on. The oily vehicle includes, among others, sesame oil, soybean oil, etc. and, as cosolvents or solubilizers, benzyl benzoate, benzyl alcohol, etc. can be employed. The injections so prepared are filled into appropriate ampules.

For use as a prophylactic or therapeutic agent for osteoporosis, the useful daily dosage of compound (I) or a salt thereof for oral administration is estimated to be 1 to 500 mg and preferably 10 to 200 mg.

The method for estimating the bone resorption inhibitory activity, and hence the therapeutic effect on osteoporosis, of compound (I) and the results of assessments are presented below.

Prophylactic and Therapeutic Effect on Osteoporosis

The test compound was administered intraperitoneally to 6-week-old Sprague-Dawley rats for 2 days. On the day following the last administration (third day), right sciatic neurotomy was performed and the bilateral tibias were removed on the 17th day. The proximal half of each tibia was cut off at right angles with its major axis, dried at 110° C. for 6 hours and, then, weighed to find dry weights.

The mean ±S.E. of the values for 6 animals per group was calculated. The results are shown in Tables 1 and 2.

TABLE 1

| Group | Daily dose (mg/kg) | Dry weight (mg) | |
|---|---|---|---|
| | | Right tibia | Left tibia |
| Sham operation control group | 0 | 105.4 ± 3.6** | 109.8 ± 3.4 |
| Operation control group | 0 | 81.5 ± 2.5 | 109.0 ± 2.5 |
| Compound (Example 8) treatment group | 1 | 147.6 ± 6.7** | 158.8 ± 6.1** |
| Compound (Example 7) treatment group | 1 | 134.1 ± 11.6** | 148.8 ± 10.3* |

Significant difference from operation control group: *$p < 0.05$ **$p < 0.01$

TABLE 2

| Group | Daily dose (mg/kg) | Dry weight (mg) | |
|---|---|---|---|
| | | Right tibia | Left tibia |
| Sham operation control group | 0 | 112.5 ± 2.9** | 113.3 ± 3.1 |
| Operation control group | 0 | 86.2 ± 4.1 | 107.3 ± 5.2 |
| Compound (Example 46) treatment group | 1 | 131.9 ± 5.8** | 151.8 ± 5.5** |

Significant difference from operation control group: **$p < 0.01$

REFERENCE EXAMPLE 1

A mixture of phenol (3.0 g), N-(4-bromobutyl)phthalimide (9.0 g), potassium carbonate (4.4 g) and N,N-dimethylformamide (DMF) (50 ml) was stirred at 100° C. for 4 hours. The reaction mixture was poured into water and extracted with ethyl acetate. The ethyl acetate layer was washed with water and dried (MgSO4), then the solvent was distilled off under reduced pressure to give 4-(4-phenoxybutyl)phthalimide (8.1 g, 87%). Recrystallization of the product from acetone gave colorless prisms, m.p.102° C. to 103° C.

REFERENCE EXAMPLES 2 AND 3

By substantially the same procedure as Reference Example 1, compounds shown in Table 3 were obtained.

TABLE 3

| Ref. Ex. No. | A– | n | Yield (%) | m.p. (°C.) | Recrystallization solvent |
|---|---|---|---|---|---|
| 2 | phenyl | 3 | 73 | 86–87 | acetone-isopropyl ether |
| 3 | 4-chlorophenyl | 4 | 77 | 120–121 | ethanol |

REFERENCE EXAMPLE 4

A mixture of 2-hydroxypyridine (6.0 g), N-(4-bromobutyl)phthalimide (17.8 g), potassium carbonate (8.7 g) and N,N-dimethylformamide (DMF) (80 ml) was stirred at 100° C. for 3 hours. The reaction mixture was poured into water and extracted with ethyl acetate. The ethyl acetate layer was washed with water and dried (MgSO₄), then the solvent was distilled off under reduced pressure. The oily residue was subjected to a silica gel column chromatography. From the fraction eluted with chloroform-ethyl acetate (4:1 v/v), N-[4-(2-pyridyloxy)butyl]phthalimide (4.4 g, 23%) was obtained Recrystallization of the product from ether gave colorless prisms, m.p. 77° C. to 78° C.

REFERENCE EXAMPLE 5

A mixture of N-(4-phenoxybutyl)phthalimide (7.8 g), hydrazine hydrate (7 ml) and ethanol (150 ml) was stirred for one hour under reflux. Crystalline precipitate was filtered off, then the filtrate was concentrated under reduced pressure to give 4-phenoxybutylamine (4.2 g, 95%) as an oily product.

NMR (in CDCl₃, δ ppm): 1.53–1.90 (4H,m), 2.77 (2H,t,J=7 Hz), 3.98 (2H,t,J=7 Hz), 6.85–6.99 (3H,m), 7.22–7.34 (2H,m).

REFERENCE EXAMPLES 6–8

By substantially the same procedure as Reference Example 5, compounds shown in Table 4 were obtained.

TABLE 4

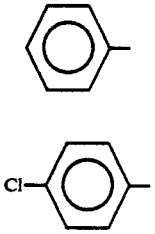

| Ref. Ex. No. | A– | n | Yield (%) | NMR(in CDCl₃, δ ppm) |
|---|---|---|---|---|
| 6 | phenyl | 3 | 85 | 1.82(2H, s), 1.94(2H, m), 2.92(2H, t, J=7Hz), 4.05(2H, t, J=7Hz), 6.87–6.99 (3H, m), 7.23–7.32(2H, m). |
| 7 | 4-chlorophenyl | 4 | 95 | 1.39(2H, s), 1.57–1.68(2H, m), 1.75–1.89 (2H, m), 2.77(2H, t, J=7Hz), 3.95(2H, t, J=6Hz), 6.82(2H, d, J=9Hz), 7.23(2H, d, J=9Hz). |
| 8 | 2-pyridyl | 4 | 94 | 1.5–1.9(6H, m), 2.77(2H, t, J=7Hz), 4.31 (2H, t, J=7Hz), 6.72(1H, ddd, J=8, 1 and 1Hz), 6.85(1H, ddd, J=7, 5 and 1Hz), 7.56(1H, ddd, J=8, 7 and 2Hz), 8.15(1H, J=5, 2 and 1Hz). |

REFERENCE EXAMPLES 9–21

By substantially the same procedure as Reference Example 1, compounds shown in Table 5 were obtained.

TABLE 5

A—O—(CH₂)$_n$—N(phthalimide)

| Ref. Ex. No. | A— | n | Yield (%) | m.p. (°C.) | Recrystallization solvent |
|---|---|---|---|---|---|
| 9 | phenyl | 5 | 80 | 72–73 | ethyl acetate-hexane |
| 10 | 4-CH₃O-phenyl | 4 | 41 | 61–62 | acetone-isopropyl ether |
| 11 | 4-CH₃-phenyl | 4 | 48 | 72–73 | isopropyl ether |
| 12 | 1,3-benzodioxol-5-yl | 4 | 68 | 112–113 | ethanol |
| 13 | 2-naphthyl | 4 | 68 | 127–128 | ethyl acetate |
| 14 | 6-methylpyridin-2-yl | 4 | 52 | 49–50 | ether-hexane |
| 15 | 5-chloropyridin-2-yl | 4 | 38 | 145–146 | chloroform-hexane |
| 16 | pyridin-2-yl | 3 | 12 | 93–94 | chloroform-hexane |
| 17 | pyrimidin-2-yl | 4 | 84 | 83–84 | chloroform-hexane |
| 18 | pyrimidin-2-yl | 3 | 62 | 149–150 | chloroform-hexane |
| 19 | pyrazin-2-yl | 4 | 88 | 110–111 | ethanol |

TABLE 5-continued

A—O—(CH₂)ₙ—N(phthalimide)

| Ref. Ex. No. | A— | n | Yield (%) | m.p. (°C.) | Recrystallization solvent |
|---|---|---|---|---|---|
| 20 | 2-methylquinolin-yl | 4 | 87 | 108–109 | ethanol |
| 21 | 3-methylquinoxalin-yl | 4 | 43 | 117–118 | chloroform-hexane |

REFERENCE EXAMPLES 22–34

By substantially the same procedure as Reference Example 5, compounds shown in Tables 6 and 7 were obtained.

TABLE 6

A—O—(CH₂)ₙ—NH₂

| Ref. Ex. No. | A— | n | Yield (%) | NMR(in CDCl₃, δ ppm) |
|---|---|---|---|---|
| 22 | phenyl | 5 | 92 | 1.39(2H, s), 1.45–1.55(4H, m), 1.81(2H, quintet, $J=7Hz$), 2.73 (2H, t, $J=7Hz$), 3.97(2H, t, $J=6Hz$), 6.90(2H, dd, $J=9$ and 1Hz), 6.93 (1H, dt, $J=9$ and 7Hz), 7.28(2H, dd, $J=9$ and 7Hz). |
| 23 | 4-CH₃O-phenyl | 4 | 92 | 1.50(2H, s), 1.53–1.88(4H, m), 2.77(2H, t, $J=7Hz$), 3.77(3H, s), 3.93(2H, t, $J=7Hz$), 6.83(4H, s). |
| 24 | 4-CH₃-phenyl | 4 | 96 | 1.44(2H, s), 1.53–1.98(4H, m), 2.29(3H, s), 2.77(2H, t, $J=7Hz$), 3.95(2H, t, $J=7Hz$), 6.80(2H, d, $J=9Hz$), 7.08(2H, d, $J=9Hz$). |
| 25 | 3,4-methylenedioxyphenyl | 4 | 73 | 1.45(2H, s), 1.52–1.68(2H, m), 1.72–1.87(2H, m), 2.76 (2H, t, $J=7Hz$), 3.90(2H, t, $J=6Hz$), 5.91(2H, s), 6.31(2H, dd, $J=8$ and 2Hz), 6.49(1H, d, $J=2Hz$), 6.70 (1H, d, $J=8Hz$). |
| 26 | naphthyl | 4 | 81 | 1.45(2H, s), 1.58–1.98(4H, m), 2.80(2H, t, $J=7Hz$), 4.10(2H, t, $J=7Hz$), 7.10–7.18(2H, m), 7.27–7.47(2H, m), 7.67–7.80(3H, m). |
| 27 | 2,6-dimethylpyridinyl | 4 | 98 | 1.49(2H, s), 1.56–1.89(4H, m), 2.43(3H, s), 2.77(2H, t, $J=7Hz$), 4.27(2H, t, $J=7Hz$), 6.50(1H, d, $J=8Hz$), 6.69(1H, d, $J=7Hz$), 7.44 (1H, dd, $J=8$ and 7Hz). |

TABLE 6-continued $$\text{(A)} - O-(CH_2)_n-NH_2$$

| Ref. Ex. No. | (A)— | n | Yield (%) | NMR (in CDCl$_3$, δ ppm) |
|---|---|---|---|---|
| 28 | 5-Cl-pyridin-2-yl | 4 | 60 | 1.51–1.84(6H, m), 2.76(2H, t, J=7Hz), 4.28(2H, t, J=7Hz), 6.08(1H, d, J=9Hz), 7.51(1H, dd, J=9 and 3 Hz), 8.08(1H, d, J=3Hz). |

TABLE 7

| Ref. Ex. No. | (A)— | n | Yield (%) | NMR (in CDCl$_3$, δ ppm) |
|---|---|---|---|---|
| 29 | pyridin-2-yl | 3 | 97 | 1.86(2H, s), 1.92(2H, quintet, J=7Hz), 2.88(2H, t, J=7Hz), 4.38(2H, t, J=7Hz), 6.73(1H, ddd, J=8, 1 and 1Hz), 6.86(1H, ddd, J=7, 5 and 1Hz), 7.57(1H, ddd, J=8, 7 and 2Hz), 8.14(1H, ddd, J=5, 2 and 1Hz). |
| 30 | pyrimidin-2-yl | 4 | 85 | 1.44(2H, s), 1.57–1.94(4H, m), 2.78(2H, t, J=7Hz), 4.38(2H, t, J=7Hz), 6.93(1H, t, J=5Hz), 8.52(2H, d, J=5Hz). |
| 31 | pyrimidin-2-yl | 3 | 37 | 1.44(2H, s), 1.97(2H, qunitet, J=7Hz), 2.92(2H, t, J=7Hz), 4.46(2H, t, J=7Hz), 6.93(1H, t, J=5Hz), 8.51(2H, d, J=5Hz). |
| 32 | pyrazin-2-yl | 4 | 85 | 1.53–1.92(6H, m), 2.77(2H, t, J=7Hz), 4.33(2H, t, J=7Hz), 8.06(1H, dd, J=3 and 1Hz), 8.10(1H, d, J=3Hz), 8.21(1H, d, J=1Hz). |
| 33 | quinolin-2-yl | 4 | 84 | 1.47(2H, s), 1.56–1.94(4H, m), 2.78(2H, t, J=7Hz), 4.49(2H, t, J=7Hz), 6.87(1H, d, J=9Hz), 7.35(1H, ddd, J=8, 7 and 1 Hz), 7.60(1H, ddd, J=8, 7 and 2 Hz), 7.69(1H, dd, J=8 and 2Hz), 7.82(1H, dd, J=8 and 2Hz), 7.95 (1H, d, J=9Hz). |
| 34 | quinoxalin-2-yl | 4 | 87 | 1.46(2H, s), 1.58–1.98(4H, m), 2.81(2H, t, J=7Hz), 4.51(2H, t, J=7 Hz), 7.56(1H, ddd, J=8, 7 and 2 Hz), 7.67(1H, ddd, J=8, 7 and 2 Hz), 7.82(1H, dd, J=8 and 2Hz), 8.01(1H, dd, J=8 and 2Hz), 8.46 (1H, s). |

EXAMPLE 1

A mixture of 4-phenoxybutylamine (4.15 g), ethyl orthoformate (5.6 g) and diethyl phosphite [HP(O)(OC$_2$H$_5$)$_2$] (13.9 g) was stirred for two hours at 150° C. The reaction mixture was concentrated under reduced pressure. The oily residue was subjected to a silica gel column chromatography. From the fraction eluted with chloroform-ethyl acetate-methanol (20:20:1, v/v), tetraethyl 4-phenoxybutylaminomethylenebisphosphonate (3.6 g, 32%) was obtained as an oily product.

NMR(in CDCl$_3$, δ ppm): 1.35 (12H,t,J=7 Hz), 1.50–2.10 (4H,m), 2.92 (2H,t,J=7 Hz), 3,27 (1H,t,J=22 Hz), 3.97 (2H,t,J=7 Hz), 4.10–4.35 (8H,m), 6.85–6.99 (3H,m), 7.22–7.35 (2H,m).

EXAMPLES 2–4

By substantially the same procedure as Example 1, compounds shown in Table 8 were obtained.

TABLE 8

$$\text{A}-\text{O}-(CH_2)_n-NH-CH\begin{matrix}P(O)(OC_2H_5)_2\\P(O)(OC_2H_5)_2\end{matrix}$$

| Ex. No. | A— | n | Yield (%) | NMR(in CDCl$_3$, δ ppm) |
|---|---|---|---|---|
| 2 | phenyl | 3 | 34 | 1.33(12H, t, J=12Hz), 1.95(2H, m), 3.05 (2H, t, J=7Hz), 3.27(1H, t, J=22Hz), 4.05(2H, t, J=7Hz), 4.1–4.3(8H, m), 6.86–6.97(3H, m), 7.22–7.32(2H, m). |
| 3 | 4-chlorophenyl | 4 | 34 | 1.35(12H, t, J=7Hz), 1.59–1.70(2H, m), 1.67(1H, s), 1.80–1.84(2H, m), 2.91(2H, t, J=7Hz), 3.26(1H, t, J=22Hz), 3.94 (2H, t, J=6Hz), 4.14–4.30(8H, m), 6.81 (2H, d, J=9Hz), 7.22(2H, d, J=9Hz). |
| 4 | 2-pyridyl | 4 | 32 | 1.35(12H, t, J=12Hz), 1.5–1.9(4H, m), 2.91(2H, t, J=7Hz), 3.28(1H, t, J=22Hz), 4.11–4.37(10H, m), 6.72(1H, ddd, J=8, 1 and 1Hz), 6.85(1H, ddd, J=7, 5 and 1Hz), 7.56(2H, ddd, J=8, 7 and 2Hz), 8.14(1H, J=5, 2 and 1Hz). |

EXAMPLE 5

A mixture of tetraethyl 4-phenoxybutylaminomethylenebisphosphonate (1.37 g) and concentrated hydrochloric acid (20 ml) was heated for two hours under reflux. The reaction mixture was concentrated under reduced pressure. The concentrate was treated with water to give 4-phenoxybutylaminomethylenebisphosphonic acid (0.549 g, 53%), m.p. 206° C. to 208° C.

NMR (in d$_6$-DMSO, δ ppm): 1.60–1.95 (4H,m), 3.23 (2H,t,J=7 Hz), 3.42 (1H,t,J=18 Hz), 3.94 (2H,t,J=7 Hz), 6.86–6.97 (3H,m), 7.20–7.33 (2H,m).

Elemental Analysis for C$_{11}$H$_{19}$NO$_7$P$_2$: Calcd.: C, 38.95; H, 5.65; N, 4.13; Found: C, 39.24; H, 5.84; N, 3.99.

EXAMPLE 6

By substantially the same procedure as Example 5, 3-phenoxypropylaminomethylenebisphosphonic acid hemihydrate was obtained, m.p. 226° C. to 227° C.

NMR (in d$_6$-DMSO, δ ppm): 2.07–2.27 (2H,m), 3.38 (2H,t,J=7 Hz), 3.51 (1H,t,J=18 Hz), 4.02 (2H,t,J=7 Hz), 6.88–6.99 (3H,m), 7.22–7.33 (2H,m).

Elemental Analysis for C$_{10}$H$_{17}$NO$_7$P$_2$.1/2H$_2$O: Calcd.: C, 35.94; H, 5.43; N, 4.19; Found: C, 35,80; H, 5.68; N, 4.02.

EXAMPLE 7

A mixture of tetraethyl 4-(2-pyridyloxy)-butylaminomethylenebisphosphonate (0.85 g) and conc. hydrochloric acid (10 ml) was heated for 2 hours under reflux. The reaction mixture was concentrated under reduced pressure. The concentrate was treated with methanol to give a solid matter, which was recrystallized from water-methanol to give 4-(2-pyridyloxy)-butylaminomethylenebisphosphonic acid hydrochloride hemihydrate (0.471 g, 65%), m.p. 155° C. to 157° C.

NMR (in D$_2$O, δ ppm): 1.93–2.12 (4H,m), 3.52 (2H,t,J=7 Hz), 3.57 (1H,t,J=18 Hz), 4.54 (2H,t,J=7 Hz), 7.44–7.55 (2H,m), 8.28 (1H,d,J=6 Hz), 8.45 (1H,t,J=9 Hz).

Elemental Analysis for C$_{10}$H$_{18}$N$_2$O$_7$P$_2$.HCl.1/2H$_2$O: Calcd: C, 31.14; H, 5.23; N, 7.26; Found: C, 31.05; H, 5.70; N, 7.16.

EXAMPLE 8

4-Phenoxybutylaminomethylenebisphosphonic acid (0.54 g) was suspended in methanol (20 ml), to which was added a methanol solution of sodium methoxide (28%, 0.782 g), and the mixture was stirred for 3 hours at room temperature. The reaction mixture was concentrated under reduced pressure. The concentrate was treated with acetone to give a solid matter, which was recrystallized from water-methanol to give 4-phenoxybutylaminomethylenebisphosphonic acid disodium salt 1.5 hydrate (0.56 g, 85%), m.p.>300° C.

NMR (in D$_2$O, δ ppm): 1.86–1.99 (4H,m), 3.05 (1H,t,J=16 Hz), 3.44 (2H,t,J=7 Hz), 4.15 (2H,t,J=7 Hz), 7.01–7.11 (3H,m), 7.33–7.45 (2H,m).

Elemental Analysis for C$_{11}$H$_{17}$NO$_7$P$_2$Na$_2$.1.5H$_2$O: Calcd.: C, 32.21; H, 4.91; N, 3.41; Found: C, 32.02; H, 4.90; N, 3.26.

EXAMPLE 9

By substantially the same procedure as Example 8, 3-phenoxypropylaminomethylenebisphosphonic acid disodium salt 1.5 hydrate was obtained, m.p.>300° C.

NMR (in D$_2$O, δ ppm): 2.26 (2H,m), 3.13 (1H,t,J=16 Hz), 3.60 (2H,t,J=7 Hz), 4.24 (2H,t,J=7 Hz), 7.02–7.14 (3H,m), 7.34–7.45 (2H,m).

Elemental Analysis for C$_{10}$H$_{15}$NO$_7$P$_2$Na$_2$.1.5H$_2$O: Calcd.: C, 30.32; H, 4.58; N, 3.54.; Found: C, 30.05; H, 4.66; N, 3.43.

EXAMPLE 10

To a solution of tetraethyl 4-(4chlorophenoxy)-butylaminoamethylenebisphonate (5.9 g) in acetonitrile (90 ml) was added bromotrimethylsilane (11.2 g). The mixture was stirred for 15 hours at room temperature. To the reaction mixture was added water (3 ml), which was concentrated under reduced pressure. The residual oily product was dissolved in methanol (50 ml), to which was added a methanol solution of sodium methoxide (28%, 14.2 ml), followed by processing with ether (150 ml), then resulting precipitate was collected by filtration. Recrystallization from water-methanol gave 4-(4-chlorophenoxy)butylaminomethylenebisphosphonic acid tetrasodium salt (2.56 g, 42%), m.p.>300° C.

NMR (in D$_2$O, δ ppm): 1.90 (4H,m), 3.01 (1H,t,J=16 Hz), 3.40 (2H,s), 4.11 (2H,s), 6.99 (2H,d,J=9 Hz), 7.35 (2H,d,J=9 Hz).

Elemental Analysis for C$_{11}$H$_{14}$NO$_7$P$_2$ClNa$_4$.1/2-H$_2$O.CH$_3$OH: Calcd.: C, 28.67; H, 3.81; N, 2.79; Found: C, 28.92; H, 4.09; N, 3.03.

EXAMPLES 11-23

By substantially the same procedure as Example 1, compounds shown in Tables 9 and 10 were obtained.

TABLE 9

$$\text{A} - \text{O}-(\text{CH}_2)_n-\text{NH}-\text{CH} \begin{array}{c} \text{P(O)(OC}_2\text{H}_5)_2 \\ \text{P(O)(OC}_2\text{H}_5)_2 \end{array}$$

| Example No. | A— | n | Yield (%) | NMR(in CDCl$_3$, δ ppm) |
|---|---|---|---|---|
| 11 | phenyl— | 5 | 37 | 1.35(12H, t, J=7Hz), 1.50-1.83(7H, m), 2.87(2H, t, J=6Hz,), 3.25(1H, t, J=22Hz), 3.95(2H, t, J=6Hz), 4.14-4.30 (8H, m), 6.88(2H, dd, J=9 and 1Hz), 6.93(1H, tt, J=7 and 1Hz), 7.27(2H, dd, J=9 and 7Hz). |
| 12 | CH$_3$O-phenyl— | 4 | 31 | 1.35(12H, t, J=7Hz), 1.58-1.90(4H, m), 2.91(2H, t, J=7Hz,), 3.27(1H, t, J=22Hz), 3.77(3H, s), 3.91(2H, t, J=7Hz), 4.12-4.30(8H, m), 6.82(4H, s). |
| 13 | CH$_3$-phenyl— | 4 | 33 | 1.34(12H, t, J=7Hz), 1.55-1.90(4H, m), 2.28(3H, s), 2.91(2H, t, J=7Hz,), 3.27 (1H, t, J=22Hz), 3.93(2H, t, J=7Hz), 4.13-4.32(8H, m), 6.78(2H, d, J=9Hz), 7.06(2H, d, J=9Hz). |
| 14 | methylenedioxyphenyl— | 4 | 30 | 1.35(12H, t, J=7Hz), 1.58-1.81(5H, m), 2.90(2H, t, J=7Hz,), 3.26(1H, t, J=22Hz), 3.89(2H, t, J=6Hz), 4.14-4.29 (8H, m), 5.91(2H, s), 6.31(1H, dd, J=9 and 3Hz), 6.48(1H, d, J=2Hz), 6.70 (1H, d, J=9Hz). |
| 15 | naphthyl— | 4 | 52 | 1.35(12H, t, J=7Hz), 1.60-2.00(4H, m), 2.95(2H, t, J=7Hz,), 3.29(1H, t, J=22Hz), 4.09(2H, t, J=7Hz), 4.12-4.32 (8H, m), 7.08-7.16(2H, m), 7.27-7.48 (2H, m), 7.68-7.80(3H, m). |
| 16 | 6-methylpyridin-2-yl— | 4 | 32 | 1.34(12H, t, J=7Hz), 1.55-1.90(4H, m), 2.43(3H, s), 2.91(2H, t, J=7Hz,), 3.27 (1H, t, J=22Hz), 4.03-4.32(10H, m), 6.50(1H, d, J=8Hz), 6.70(1H, d, J=7Hz), 7.44(1H, dd, J=8 and 7Hz). |
| 17 | 5-chloropyridin-2-yl— | 4 | 52 | 1.35(12H, t, J=7Hz), 1.60-2.00(4H, m), 2.95(2H, t, J=7Hz,), 3.29(1H, t, J=22Hz), 4.09(2H, t, J=7Hz), 4.12-4.32 (8H, m), 7.08-7.16(2H, m), 7.27-7.48 (2H, m), 7.68-7.7.80(3H, m). |

TABLE 10

| Example No. | A— | n | Yield (%) | NMR(in CDCl$_3$, δ ppm) |
|---|---|---|---|---|
| 18 | pyridin-2-yl— | 3 | 16 | 1.34(12H, t, J=7Hz), 1.95(2H, quintet, J=6Hz), 3.03(2H, t, J=6Hz,), 3.29(1H, t, J=22Hz), 4.10-4.30(8H, m), 4.37 (2H, t, J=6Hz), 6.73(1H, ddd, J=8.1 and 1Hz), 6.86(1H, ddd, J=7.5 and 1Hz), 7.57(1H, ddd, J=8, 7 and 2Hz), 8.14(1H, ddd, J=5, 2 and 1Hz). |

TABLE 10-continued

| Example No. | A— | n | Yield (%) | NMR(in CDCl₃, δ ppm) |
|---|---|---|---|---|
| 19 | pyrimidin-2-yl | 4 | 20 | 1.35(12H, t, J=7Hz), 1.59-1.95(4H, m), 2.92(2H, t, J=7Hz,), 3.28(1H, t, J=22Hz), 4.11-4.30(8H, m), 4.37(2H, t, J=7Hz), 6.93(1H, t, J=5Hz), 8.51(2H, d, J=5Hz). |
| 20 | pyrimidin-2-yl | 3 | 31 | 1.34(12H, t, J=7Hz), 1.99(2H, quintet, J=7Hz,), 3.05(2H, t, J=7Hz), 3.29(1H, t, J=22Hz), 4.14-4.30(8H, m), 4.44(2H, t, J=6Hz), 6.92(1H, t, J=5Hz), 8.50(2H, d, J=5Hz). |
| 21 | pyrazin-2-yl | 4 | 25 | 1.35(12H, t, J=7Hz), 1.59-1.99(4H, m), 2.92(2H, t, J=7Hz,), 3.27(1H, t, J=22Hz), 4.15-4.32(8H, m), 4.33(2H, t, J=6Hz), 8.07(1H, dd, J=3 and 1Hz), 8.11(2H, d, J=3Hz), 8.21(1H, d, J=1Hz). |
| 22 | quinolin-2-yl | 4 | 33 | 1.34(12H, t, J=7Hz), 1.62-1.96(4H, m), 2.94(2H, t, J=7Hz,), 3.28(1H, t, J=22Hz), 4.15-4.27(8H, m), 4.48(2H, t, J=6Hz), 6.88(1H, d, J=9Hz), 7.36(1H, ddd, J=8, 7 and 1Hz), 7.60(1H, ddd, J=8, 7 and 1Hz), 7.70(1H, dd, J=8 and 1Hz), 7.81(1H, dd, J=8 and 1Hz), 7.97(1H, d, J=8Hz). |
| 23 | quinoxalin-2-yl | 4 | 31 | 1.35(12H, t, J=7Hz), 1.65-1.96(4H, m), 2.95(2H, t, J=7Hz), 3.28(1H, t, J=22Hz), 4.14-4.30(8H, m), 4.49(2H, t, J=7Hz), 7.57(1H, ddd, J=8, 7 and 2Hz), 7.67(1H, ddd, J=8, 7 and 2Hz), 7.82(1H, dd, J=8 and 2Hz), 8.02(1H, dd, J=8 and 2Hz). |

EXAMPLE 24

By substantially the same procedure as Example 10, 5-phenoxypentylaminomethylenebisphosphonic acid disodium salt trihydrate was obtained, which was recrystallized form water-methanol. m.p.>300° C.

Elemental Analysis for $C_{12}H_{19}NO_7P_2Na_2.3H_2O$: Calcd.: C, 31.94; H, 5.58; N, 3.10; Found: C, 32.04; H, 5.39; N, 2.96.

EXAMPLE 25

5-Phenoxypentylaminomethylenebisphosphonic acid disodium salt trihydrate (1.0 g) was dissolved in water (5 ml). The solution was processed with a column of CG-50 (H type, 32 ml). The solid matter obtained from the acidic portion eluted with water was recrystallized from water-methanol to afford 5-phenoxypentylaminomethylenebisphosphonic acid monosodium salt hemihydrate (0.58 g, 68%) as colourless prisms, m.p.>300° C.

Elemental Analysis for $C_{12}H_{20}NO_7P_2Na.1/2H_2O$: Calcd.: C, 37.51; H, 5.51; N, 3.65; Found: C, 37,62; H, 5.53; N, 3.55.

EXAMPLES 26-30

By substantially the same procedure as Example 5, compounds shown in Table 11 were obtained.

EXAMPLES 31-33

By substantially the same procedure as Example 8, compounds shown in Table 12 were obtained.

TABLE 11

$$\text{(A)}-O-(CH_2)_4-NH-CH \begin{matrix} P(O)(OH)_2 \\ P(O)(OH)_2 \end{matrix}$$

| Example No. | A— | Yield (%) | m.p. (°C.) | Recrystallization solvent | Molecular formula |
|---|---|---|---|---|---|
| 26 | 4-CH₃O-phenyl | 73 | 188-189 | Water-methanol | $C_{12}H_{21}NO_8P_2.H_2O$ |
| 27 | 4-CH₃-phenyl | 66 | 204-206 | Water-methanol | $C_{12}H_{21}NO_7P_2$ |

TABLE 11-continued $$A\!-\!O\!-\!(CH_2)_4\!-\!NH\!-\!CH\!\begin{array}{c}P(O)(OH)_2\\P(O)(OH)_2\end{array}$$

| Example No. | A— | Yield (%) | m.p. (°C.) | Recrystallization solvent | Molecular formula |
|---|---|---|---|---|---|
| 28 | 2-naphthyl | 64 | 235–236 | Water-methanol | $C_{15}H_{21}NO_7P_2$ |
| 29 | 5-chloropyridin-2-yl | 38 | 167–168 | Water-ethanol | $C_{10}H_{17}N_2O_7ClP_2 \cdot \tfrac{1}{2}H_2O$ |
| 30 | quinolin-2-yl | 49 | 134–135 | Water-methanol | $C_{14}H_{20}N_2O_7P_2 \cdot 3H_2O$ |

TABLE 12

$$A\!-\!O\!-\!(CH_2)_4\!-\!NH\!-\!CH\!\begin{array}{c}P(O)(OH)(ONa)\\P(O)(OH)(ONa)\end{array}$$

| Example No. | A— | Yield (%) | m.p. (°C.) | Recrystallization solvent | Molecular formula |
|---|---|---|---|---|---|
| 31 | $CH_3O$-$C_6H_4$- | 56 | >300 | Water-methanol | $C_{12}H_{19}NO_8Na_2P_2 \cdot 2H_2O$ |
| 32 | $CH_3$-$C_6H_4$- | 75 | >300 | Water-methanol | $C_{12}H_{19}NO_7Na_2P_2 \cdot 2H_2O$ |
| 33 | 2-naphthyl | 62 | >300 | Water-methanol | $C_{15}H_{19}NO_7Na_2P_2 \cdot \tfrac{1}{2}H_2O$ |

EXAMPLE 34

By substantially the same procedure as Example 10, 4-(3,4-methylenedioxyphenoxy)butylaminomethylenebisphosphonic acid trisodium salt monohydrate was obtained, which was recrystallized from water-methanol. m.p.>300° C.

Elemental Analysis for $C_{12}H_{16}NO_9P_2Na_3 \cdot H_2O$: Calcd.: C, 30.85; H, 3.88; N, 3.00; Found: C, 31.07; H, 4.02; N, 2.99.

EXAMPLES 35 AND 36

By substantially the same procedure as Example 7, compounds shown in Table 13 were obtained.

TABLE 10

$$\text{A}—\text{O}—(\text{CH}_2)_n—\text{NH}—\text{CH}\begin{array}{c}\diagup \text{P(O)(OH)}_2 \\ \diagdown \text{P(O)(OH)}_2\end{array}$$

| Ex. No. | A— | n | Yield (%) | m.p. (°C.) | Recrystallization solvent | Molecular formula |
|---|---|---|---|---|---|---|
| 35 | 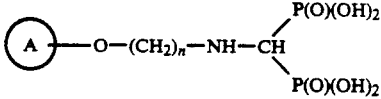 | 4 | 78 | 148–150 | Ethanol | $C_{11}H_{20}N_2O_7P_2 \cdot HCl \cdot 2H_2O$ |
| 36 |  | 3 | 69 | 172–173 | Water-ethanol | $C_9H_{16}N_2O_7P_2 \cdot HCl \cdot 2H_2O$ |

EXAMPLE 37

To a solution of tetraethyl 4-(2-pyrimidinyloxy)-butylaminomethylenebisphosphonate (5.0 g) in acetonitrile (90 ml) was added bromotrimethylsilane (10.1 g), and the mixture was stirred for 16 hours at room temperature. To the reaction mixture was added water (2 ml), which was stirred for one hour at room temperature, followed by concentration under reduced pressure. The concentrate was suspended in water (5 ml), to which was added an aqueous solution of sodium hydroxide (1N, 11.7 ml). To the reaction mixture was added ethanol, then precipitating crystals were collected by filtration, followed by recrystallization from water-acetone to give 4-(2-pyrimidinyloxy)-butylaminomethylenebisphosphonic acid monosodium salt dihydrate (1.4 g, 31%) as colorless crystals, m.p.>300° C.

Elemental Analysis for $C_9H_{16}N_3O_7P_2Na \cdot 2H_2O$: Calcd.: C, 27.08; H, 5.05; N, 10.53; Found: C, 27.31; H, 5.02; N, 10.60.

EXAMPLE 38

By substantially the same procedure as Example 37, 3-(2-pyrimidinyloxy)propylaminomethylenebisphosphonic acid disodium salt dihydrate was obtained, which was recrystallized from water-ethanol. m.p.>300° C.

Elemental Analysis for $C_8H_{13}N_3O_7P_2Na_2 \cdot 2H_2O$: Calcd.: C, 23.60; H, 4.21; N, 10.32; Found: C, 23.70; H, 4.35; N, 10.05.

EXAMPLE 39

By substantially the same procedure as Example 37, 4-(2-pyrazinyloxy)butylaminomethylenebisphosphonic acid monosodium salt 2.5 hydrate was obtained, which was recrystallized from water-acetone. m.p.>300° C.

Elemental Analysis for $C_9H_{16}N_3O_7P_2Na \cdot 2.5H_2O$: Calcd.: C, 26.48; H, 5.19; N, 10.29; Found: C, 26.45; H, 4.88; N, 10.29.

EXAMPLE 40

By substantially the same procedure as Example 37, 4-(2-quinoxalinyloxy)butylaminomethylenebisphosphonic acid monosodium trihydrate was obtained, which was recrystallized from water-ethanol. m.p.>300° C.

Elemental Analysis for $C_{13}H_{18}N_3O_7P_2Na \cdot 3H_2O$: Calcd.: C, 33.41; H, 5.18; N, 8.99; Found: C, 33.23; H, 5.28; N, 8.90.

EXAMPLE 41

A mixture of tetraethyl 4-(2-pyridyloxy)-butylaminomethylenebisphosphonate (5.5 g) and acetic anhydride (12.3 g) was stirred for 52 hours at room temperature. The reaction mixture was concentrated under reduced pressure, then the concentrate was subjected to a silica gel column chromatography, followed by elution with ethyl acetate-ethanol (50:1 v/v). From the fraction thus eluted, tetraethyl N-acetyl-4-(2-pyridyloxy)butylaminomethylenebisphosphonate (2.9 g, 49%) as an oily product.

NMR(in $CDCl_3$, δ ppm): 1.33(12H,t,J=7 Hz), 1.70–2.05 (4H,m), 2.19(3H,s), 3.62–3.75(2H,m), 4.10–4.30 (8H,m), 4.27(2H,t,J=6 Hz), 5.92(1H,t,J=25.5 Hz), 6.72(1H,ddd,J=8, 1 and 1 Hz), 6.85(1H,ddd,J=7, 5 and 1 Hz), 7.57(1H,ddd, J=8, 7 and 2 Hz), 8.17(1H,ddd,J=5, 2 and 1 Hz).

EXAMPLE 42

To a solution of tetraethyl N-acetyl-4-(2-pyridyloxy)-butylaminomethylenebisphosphonate (2.8 g) in acetonitrile (50 ml) was added bromotrimethylsilane (5.2 g), and the mixture was stirred for 15 hours at room temperature. To the reaction mixture was added water (1.2 ml), which was stirred for one hour at room temperature, followed by concentration under reduced pressure. The concentrate was dissolved in methanol (10 ml), to which was added a methanol solution of sodium methoxide (28%, 2.2 g). The reaction mixture was concentrated under reduced pressure. The residual crystals were collected by filtration and recrystallized from methanol-acetone to give N-acetyl-(4-2-pyridyloxy)-butylaminomethylenebisphosphonic acid disodium salt trihydrate (2.0 g, 71%) as colorless crystals, m.p. 133° C. to 135° C.

Elemental Analysis for $C_{12}H_{18}N_2O_8P_2Na_2 \cdot 3H_2O$: Calcd.: C, 30.01; H, 5.04; N, 5.83; Found: C, 29.91; H, 5.20; N, 6.02.

EXAMPLE 43

4-(2-Pyridyloxy)butylaminomethylenebisphosphonic acid hydrochloride (1.1 g) was dissolved in water (25 ml), to which was added an aqueous solution of sodium hydroxide (1N, 3 ml). To the mixture was added methanol to cause precipitation of a solid matter, which was collected by filtration and recrystallized from water-methanol to afford 4-(2-pyridyloxy)butylaminomethylenebisphosphonic acid trihydrate (0.6 g, 51%) as colorless crystals, m.p. 186° C. to 187° C.

Elemental Analysis for $C_{10}H_{18}N_2O_7P_2.3H_2O$: Calcd.: C, 30.47; H, 6.14; N, 7.11; Found: C, 30.40; H, 5.98; N, 6.93.

EXAMPLE 44

4-(2-Pyridyloxy)butylaminomethylenebisphosphonic acid hydrochloride (2.0 g) was dissolved in water (50 ml), to which was added an aqueous solution of sodium hydroxide (1N, 15.9 ml). The reaction mixture was concentrated and then dissolved in water (50 ml). To the solution was added methanol to cause precipitation of a solid matter. The solid matter was collected by filtration and washed with methanol to give 4-(2-pyridyloxy)butylaminomethylenebisphosphonic acid disodium salt monohydrate (1.3 g, 62%) as colorless crystals, m.p. >300° C.

Elemental Analysis for $C_{10}H_{16}N_2O_7P_2Na_2.H_2O$: Calcd.: C, 29.86; H, 4.51; N, 6.97; Found: C, 29.70; H, 4.74; N, 6.73.

EXAMPLE 45

A mixture of 3-methylthiopropylamine (5.47 g), ethyl orthoformate (19.27 g) and diethyl phosphite (35.91 g) was refluxed for 3 hours. The reaction mixture was concentrated under reduced pressure and the oily residue was subjected to a silica gel column chromatography. Elution with ethyl acetate-chloroform-methanol (5:5:1, v/v) gave tetraethyl 3-methylthiopropylaminomethylenebisphosphonate as an oil (8.91 g, 44%).

NMR (δ ppm in CDCl₃): 1.36 (12H, t, J=7 Hz), 1.75 (1H, s), 1.76 (2H, quintet, J=7 Hz), 2.10 (3H, s), 2.57 (2H, t, J=7 Hz), 2.95 (2H, t, J=7 Hz), 3.25 (1H, t, J=22 Hz), 4.14-4.30 (8H, m).

EXAMPLE 46

To a solution of tetraethyl 3-methylthiopropylaminomethylenebisphosphonate (5.28 g) in acetonitrile (100 ml) was added bromotrimethylsilane (12.39 g) and the mixture was stirred at room temperature for 15 hours. The reaction mixture was diluted with water (3.2 ml) and concentrated under reduced pressure. The solid residue was collected by filtration and recrystallized from water-methanol to give 3-methylthiopropylaminomethylenebisphosphonic acid hemihydrate (1.84 g, 47%). Colorless prisms, m.p. 120°-122° C.

Elemental Analysis for $C_5H_{15}NO_6S.0.5H_2O$: Calcd. C, 20.84; H, 5.60; N, 4.86; Found: C, 20.86; H, 5.91; N, 4.79.

EXAMPLES 47-57

By substantially the same procedure as Example 45, compounds shown in Tables 14 and 15 were obtained.

TABLE 14

$$R^1-X-(CH_2)_n-NHCH\begin{array}{l}P(O)(OC_2H_5)_2\\P(O)(OC_2H_5)_2\end{array}$$

| Example No. | R¹ | X | n | Yield (%) | NMR (in CDCl₃, δ ppm) |
|---|---|---|---|---|---|
| 47 | C₆H₅-CH₂CH₂— | S | 2 | 35 | 1.35(12H, t, J=7Hz), 1.72(1H, s), 2.66(2H, t, J=7Hz,), 2.73-2.94(4H, m), 3.05(2H, t, J=7Hz), 3.29(1H, t, J=22Hz), 4.14-4.31(8H, m), 7.18-7.31(5H, m). |
| 48 | (CH₃)₃C— | S | 4 | 43 | 1.31(9H, s), 1.35(12H, t, J=7Hz), 1.55-1.67(5H, m), 2.53(2H, t, J=7 Hz,), 2.85(2H, t, J=6Hz), 3.25(1H, t, J=22Hz), 4.14-4.30(8H, m). |
| 49 | CH₃— | S | 4 | 47 | 1.35(12H, t, J=7Hz), 1.50-1.75(5H, m), 2.09(3H, s), 2.53(2H, t, J=7Hz,), 2.86(2H, t, J=6Hz), 3.25(1H, t, J=22 Hz), 4.10-4.32(8H, m). |
| 50 | C₂H₅— | S | 4 | 44 | 1.25(3H, t, J=7Hz), 1.35(12H, t, J=7 Hz,), 1.50-1.75(5H, m), 2.46-2.60 (4H, m), 2.86(2H, t, J=7Hz), 3.25 (1H, t, J=22Hz), 4.10-4.30(8H, m). |
| 51 | CH₃— | S | 5 | 50 | 1.35(12H, t, J=7Hz), 1.40-1.80(7H, m), 2.48(2H, t, J=7Hz,), 2.84(2H, t, J=7Hz), 3.25(1H, t, J=22Hz), 4.10-4.30(8H, m). |

TABLE 15

| Example No. | R¹ | X | n | Yield (%) | NMR (in CDCl₃, δ ppm) |
|---|---|---|---|---|---|
| 52 | C₂H₅— | S | 5 | 46 | 1.25(3H, t, J = 7Hz), 1.35(12H, t, J = 7Hz), 1.40-1.80(7H, m), 2.48-2.60 (4H, m), 2.84(2H, t, J = 7Hz), 3.25 (1H, t, J = 22Hz), 4.10-4.30(8H, m). |
| 53 | CH₃— | O | 3 | 50 | 1.35(12H, t, J = 7Hz), 1.74(2H, quintet, J = 7Hz), 1.78(1H, s), 2.93(2H, t, J = 7Hz), 3.25(1H, t, J = 22Hz), 3.32(3H, s), 4.14-4.29 (8H, m). |
| 54 | C₂H₅— | O | 3 | 58 | 1.19(3H, t, J = 7Hz), 1.35(12H, t, J = 7Hz), 1.74(2H, quintet, J = 7Hz), 2.93(2H, t, J = 7Hz), 3.25(1H, t, J = 22Hz), 3.48(2H, t, J = 7Hz), 4.14-4.29(8H, m). |
| 55 | (CH₃)₃C— | O | 3 | 41 | 1.18(9H, s), 1.35(12H, t, J = 7Hz), 1.70(2H, quintet, J = 6Hz), 1.73(1H, s), 2.92(2H, t, J = 7Hz), 3.26(1H, t, J = 22Hz), 3.41(2H, t, J = 6Hz), 4.14-4.30(8H, m). |
| 56 | (CH₃)₃C— | O | 4 | 44 | 1.18(9H, s), 1.35(12H, t, J = 7Hz), 1.50-1.56(4H, m), 1.61(1H, s), 2.85(2H, t, J = 7Hz), 3.26(1H, t, J = 22Hz), 3.34(2H, t, J = 6Hz), 4.14-4.31(8H, m). |
| 57 | (CH₃)₃C— | O | 5 | 37 | 1.17(9H, s), 1.35(12H, t, J = 7Hz), |

TABLE 15-continued 1.42-1.56(6H, m), 1.68(1H, s),
2.83(2H, t, $J$ = 7Hz), 3.25(1H, t, $J$ = 22Hz), 3.32(2H, t, $J$ = 7Hz), 4.13-4.30(8H, m).

EXAMPLES 58-62

By substantially the same procedure as Example 45, compounds shown in Table 16 were obtained.

TABLE 16

$$R^1-X-(CH_2)_n-NHCH \begin{matrix} P(O)(OH)_2 \\ \\ P(O)(OH)_2 \end{matrix}$$

| Example No. | $R^1$ | X | n | Yield (%) | m.p. (°C.) | Molecular formula |
|---|---|---|---|---|---|---|
| 58 | $CH_3-$ | S | 4 | 73 | 218-219 | $C_6H_{17}NO_6P_2S.H_2O$ |
| 59 | $C_2H_5-$ | S | 4 | 63 | 212-213 | $C_7H_{19}NO_6P_2S$ |
| 60 | $CH_3-$ | S | 5 | 54 | 218-219 | $C_7H_{19}NO_6P_2S$ |
| 61 | $C_2H_5-$ | S | 5 | 63 | 217-218 | $C_8H_{21}NO_6P_2S$ |
| 62 | $(CH_3)_3C-$ | O | 4 | 36 | 183-184 | $C_9H_{23}NO_7P_2.\frac{1}{2}H_2O$ |

EXAMPLE 63

To a solution of tetraethyl 2-(2-phenylethylthio)ethylaminomethylenebisphosphonate (4.4 g) in acetonitrile (90 ml) was added bromotrimethylsilane (8.6 g), and the mixture was stirred for 16 hours at room temperature. The reaction mixture was diluted with water (2 ml), which was stirred for one hour at room temperature, followed by concentration under reduced pressure. The residual solid was suspended in methanol (50 ml), to which was added a methanol solution of sodium methoxide (28%, 3.2 g). To the solution was added ether to cause precipitation crystals. The crystals collected by filtration were recrystallized from water-methanol to give 2-(2-phenylethylthio)ethylaminomethylenebisphosphonic acid disodium salt 1.5 hydrate (2.0 g, 49%) as colorless crystals, m.p. > 300° C.

Elemental Analysis for $C_{11}H_{17}NO_6P_2SNa_2.1.5H_2O$: Calcd.: C, 30.99; H, 4.73; N, 3.29; Found: C, 30.80; H, 4.67; N, 3.16.

EXAMPLE 64

By substantially the same procedure as Example 63, disodium 4-tert.butylthiobutylaminomethylenebisphosphonate was obtained. Recrystallization was conducted from watermethanol. m.p. > 300° C.

Elemental Analysis for $C_9H_{21}NO_6P_2SNa_2.2.5H_2O$: Calcd.: C, 25.48; H, 6.18; N, 3.30; Found: C, 25.59; H, 6.32; N, 3.23.

EXAMPLE 65

By substantially the same procedure as Example 63, trisodium 3-methoxypropylaminomethylenebisphosphonate was obtained. Recrystallization was performed from water-methanol. m.p. > 300° C.

Elemental Analysis for $C_5H_{12}NO_7P_2Na_3.3H_2O$: Calcd.: C, 15.68; H, 4.74; N, 3.66; Found: C, 15.57; H, 4.58; N, 3.51.

EXAMPLE 66

In water (5 ml) was dissolved 3-methoxypropylaminomethylenebisphosphonic acid trisodium salt trihydrate (1.0 g), and the solution was passed through a column packed with Amberlite CG-50 (H+ type, 75 ml). Elution was conducted with water. From the acidic fraction thus eluted, 3-methoxypropylaminomethylenebisphosphonic acid monosodium salt hemihydrate (0.67 g, 87%) was obtained as colorless prisms, m.p. 277°-279° C.

Elemental Analysis for $C_5H_{14}NO_7P_2Na.1/2H_2O$: Calcd.: C, 20.42; H, 5.14; N, 4.76; Found: C, 20.64; H, 5.40; N, 4.80.

EXAMPLE 67

To a solution of tetraethyl 3-ethoxypropylaminomethylenebisphosphonate (8.3 g) in acetonitrile (100 ml) was added bromotrimethylsilane (19.6 g), which was stirred for 16 hours at room temperature. The reaction mixture was diluted with water (10 ml), which was stirred for one hour at room temperature, followed by concentration under reduced pressure. The concentrate was dissolved in methanol (20 ml), to which was added a methanol solution of sodium methoxide (28%, 30 g). To the reaction mixture was added ether to cause precipitation of a solid matter. The solid matter was collected by filtration and dissolved in water (10 ml), which was processed with a column of CG-50 (H+ type, 200 ml). From the acidic fraction eluted with water, monosodium 3-ethoxypropylaminomethylenebisphosphonate (3.8 g, 58%) was obtained. Recrystallization was performed from water-methanol. m.p. > 300° C.

Elemental Analysis for $C_6H_{16}NO_7P_2Na.1/2H_2O$: Calcd.: C, 23.39; H, 5.56; N, 4.55; Found: C, 23.32; H, 5.59; N, 4.29.

What is claimed is:

1. A compound of the formula (I):

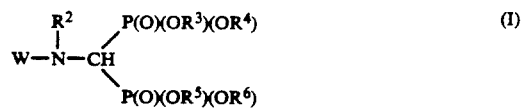

(I)

wherein W is a group of the formula:

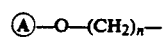

wherein Ⓐ is a phenyl, naphthyl or anthryl
each of these groups optionally being substituted with
1 to 4 substituents selected from the group consisting of
(i) halogen,
(ii) nitro,
(iii) $C_{1-7}$ straight-chain or branched alkyl or $C_{3-7}$ cycloalkyl which may be substituted with 1 to 3 substituents selected from the group consisting of halogen, hydroxyl and $C_{1-6}$ alkoxy,
(iv) hydroxyl or protected hydroxyl selected from the group consisting of $C_{1-6}$ straight-chain or branched alkoxy, $C_{4-6}$ cycloalkoxy, $C_{2-6}$ alkenyloxy, $C_{6-19}$ aralkyloxy, $C_{2-7}$ alkanoyloxy and $C_{6-14}$ aryloxy, and each of these protected hydroxyl groups optionally being substituted with 1 to 3 substituents selected from the group consisting of halogen, hydroxyl and $C_{1-6}$ alkoxy and (v) thiol or protected thiol selected from the group consisting of $C_{1-6}$ straight-chain or branched alkylthio, $C_{4-7}$ cycloalkylthio, $C_{7-19}$ aralkylthio and $C_{2-7}$ alkanoylthio, and each of the protected thiol groups optionally being substituted with 1 to 3 substituents selected from the group consisting of halogen, hydroxyl and $C_{1-6}$ alkoxy, n is an integer of 2 to 10; $R^2$ is hydrogen or $C_{1-6}$ alkylcarbonyl, $R^3$, $R^4$, $R^5$ and $R^6$ are the same or different and are hydrogen or $C_{1-4}$ alkyl, or a salt thereof.

2. A compound of claim 1 wherein (A) is a phenyl group which is unsubstituted or substituted with halogen, $C_{1-6}$ alkyl or $C_{1-6}$ alkoxy.

3. A compound of claim 1 wherein n is 3, 4 or 5.

4. A compound of claim 1 wherein n is 4.

5. A compound of claim 1 wherein n' is 4 or 5.

6. A compound of claim 1 which is 4-phenoxybutylaminomethylenebisphosphonic acid.

7. A bone resorption inhibitory composition which comprises an effective inhibitory amount of the compound of the formula (I) as claimed in claim 1 or a pharmaceutically acceptable salt thereof and a pharmaceutically acceptable carrier, diluent or excipient.

8. A composition of claim 7 which comprises 3-methylthiopropylaminomethylenebisphosphonic acid.

9. A composition of claim 7 which comprises 2-(2-phenylethylthio)ethylaminomethylenebisphosphonic acid.

* * * * *